US011039890B2

(12) United States Patent
Cole et al.

(10) Patent No.: US 11,039,890 B2
(45) Date of Patent: Jun. 22, 2021

(54) SYSTEM AND METHOD FOR TRACKING AND DETERMINING CHARACTERISTICS OF INFLATABLE MEDICAL INSTRUMENTS USING FIBER-OPTICAL REALSHAPE DATA

(71) Applicant: KONINKLIJKE PHILIPS N.V., Eindhoven (NL)

(72) Inventors: Gregory Cole, Ossining, NY (US); Paul Thienphrapa, Cambridge, MA (US); Molly Lara Flexman, Melrose, MA (US); David Paul Noonan, New York, NY (US); Neriman Nicoletta Kahya, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 557 days.

(21) Appl. No.: 15/736,854

(22) PCT Filed: Jun. 8, 2016

(86) PCT No.: PCT/EP2016/062979
§ 371 (c)(1),
(2) Date: Dec. 15, 2017

(87) PCT Pub. No.: WO2016/206975
PCT Pub. Date: Dec. 29, 2016

(65) Prior Publication Data
US 2018/0360545 A1 Dec. 20, 2018

Related U.S. Application Data

(60) Provisional application No. 62/183,942, filed on Jun. 24, 2015.

(51) Int. Cl.
*A61B 34/20* (2016.01)
*A61M 25/10* (2013.01)
(Continued)

(52) U.S. Cl.
CPC ............ *A61B 34/20* (2016.02); *A61B 5/1076* (2013.01); *A61B 5/6853* (2013.01); *A61B 90/37* (2016.02);
(Continued)

(58) Field of Classification Search
CPC ........... A61B 2017/22038; A61B 2017/22042; A61B 2017/22051; A61B 2034/2061;
(Continued)

(56) References Cited

U.S. PATENT DOCUMENTS

2007/0032818 A1 2/2007 McEwen
2012/0271339 A1 10/2012 O'Beirne et al.
(Continued)

*Primary Examiner* — Michael T Rozanski

(57) ABSTRACT

A system and method for tracking and determining characteristics of an inflatable medical instrument that is configured for interventional deployment. The system includes a guidewire that is positioned within a lumen of the inflatable medical instrument. The guidewire includes an optical fiber for a FORS system. The FORS system is configured to measure a shape of the guidewire during the interventional deployment of the inflatable medical instrument. A shape analysis module is configured to analyze the FORS data from the FORS system and determine characteristics of the inflatable medical instrument, including the diameter of the inflatable instrument, the pressurization of the instrument, whether the instrument has ruptured and the position of the inflatable instrument during an interventional procedure.

19 Claims, 12 Drawing Sheets

Empty

Inflated

Pressurized

(51) Int. Cl.
  *A61B 90/00* (2016.01)
  *A61B 5/107* (2006.01)
  *A61B 5/00* (2006.01)
  *A61M 25/09* (2006.01)
  *A61M 25/01* (2006.01)
  *A61B 17/22* (2006.01)

(52) U.S. Cl.
  CPC .... *A61M 25/09041* (2013.01); *A61M 25/104* (2013.01); *A61M 25/10184* (2013.11); *A61B 2017/22038* (2013.01); *A61B 2017/22042* (2013.01); *A61B 2017/22051* (2013.01); *A61B 2034/2061* (2016.02); *A61B 2034/2065* (2016.02); *A61B 2090/0803* (2016.02); *A61B 2090/0809* (2016.02); *A61B 2090/3614* (2016.02); *A61B 2090/373* (2016.02); *A61M 2025/0166* (2013.01); *A61M 2025/105* (2013.01); *A61M 2205/15* (2013.01); *A61M 2205/70* (2013.01)

(58) Field of Classification Search
  CPC .... A61B 2034/2065; A61B 2090/0803; A61B 2090/0809; A61B 2090/3614; A61B 2090/373; A61B 34/20; A61B 5/1076; A61B 5/6853; A61B 90/37; A61M 2025/0166; A61M 2025/105; A61M 2025/15; A61M 2025/70; A61M 25/09041; A61M 25/10184; A61M 25/104
  See application file for complete search history.

(56) References Cited

U.S. PATENT DOCUMENTS

| | | |
|---|---|---|
| 2013/0204124 A1 | 8/2013 | Duindam et al. |
| 2013/0310685 A1 | 11/2013 | Chan et al. |
| 2015/0238275 A1 | 8/2015 | Kung et al. |
| 2016/0000519 A1 | 1/2016 | Marvast |

//  SYSTEM AND METHOD FOR TRACKING AND DETERMINING CHARACTERISTICS OF INFLATABLE MEDICAL INSTRUMENTS USING FIBER-OPTICAL REALSHAPE DATA

CROSS-REFERENCE to PRIOR APPLICATIONS

This application is the U.S. National Phase application under 35 U.S.C. §371 of International Application Serial No. PCT/EP2016/062979, filed on Jun. 8, 2016, which claims the benefit of U.S. patent application No. 62/183,942, filed on Jun. 24, 2015. This application is hereby incorporated by reference herein.

BACKGROUND

Technical Field

This disclosure relates to medical devices and more particularly to a system and method for tracking an inflatable medical instrument and determining characteristics of the instrument by using Fiber-Optical RealShape™ data.

Description of the Related Art

Inflatable medical instruments are used in numerous intravascular interventional procedures for various purposes, including opening an occluded vessel, deploying a stent graft, eluting a therapeutic composition and applying pressure to a valve or anatomical structure. For example, in a balloon angioplasty procedure, a balloon catheter is used to increase the lumen diameter of a blood vessel which has become partially occluded by plaque or constriction stenosis. In this procedure, a guidewire is traditionally utilized to cross the occlusion and the catheter then follows the guidewire. A mixture of saline and contrast agent is injected into the balloon of the catheter to inflate it. During the inflation, the pressure in the balloon is carefully monitored for adverse events such as balloon rupture or vessel dissection within the body of the subject. The balloon is then held in its deployed state for a period of time ranging from seconds to minutes and the balloon is typically re-inflated multiple times to achieve successful reopening of the blood vessel. At the conclusion of the procedure, the balloon is deflated and removed from the body.

Fluoroscopy is normally implemented to properly track an inflatable medical instrument such as a balloon catheter during an angioplasty procedure. More specifically, fluoroscopy is used to navigate the balloon to the correct position within the subject as well as to monitor the balloon catheter during inflation, pressurization, and depressurization. However, a disadvantage of fluoroscopy is that it exposes the subject to harmful radiation.

SUMMARY

In accordance with the present principles, a medical system includes an inflatable medical instrument that is configured for interventional deployment. The inflatable medical instrument includes an optical fiber for a Fiber-Optical RealShape™ ("FORS") system. The FORS system is configured to measure the shape of the inflatable medical instrument during the interventional deployment. A shape analysis module is configured to analyze the FORS data and determine characteristics of the inflatable medical instrument.

In another embodiment, a medical system for tracking and determining characteristics of an inflatable medical instrument configured for interventional deployment includes an inflatable medical instrument that is configured for interventional deployment. A guidewire is positioned within a lumen of the inflatable medical instrument. The guidewire includes an optical fiber for a FORS system. FORS is configured to measure a shape of the guidewire during the interventional deployment of the inflatable medical instrument. The system further includes a workstation that features one or more processors, memory and an interface. A shape analysis module is configured to analyze FORS data from the FORS system and determine characteristics of the inflatable medical instrument.

In another embodiment, a method for tracking and determining characteristics of an inflatable medical instrument configured for interventional deployment includes the steps of positioning a guidewire within a lumen of the inflatable medical instrument, said guidewire including an optical fiber for a FORS system. A shape of the guidewire is determined during interventional deployment of the inflatable medical instrument by a FORS system. The FORS data is analyzed and characteristics of the inflatable medical instrument are determined based on the FORS data.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
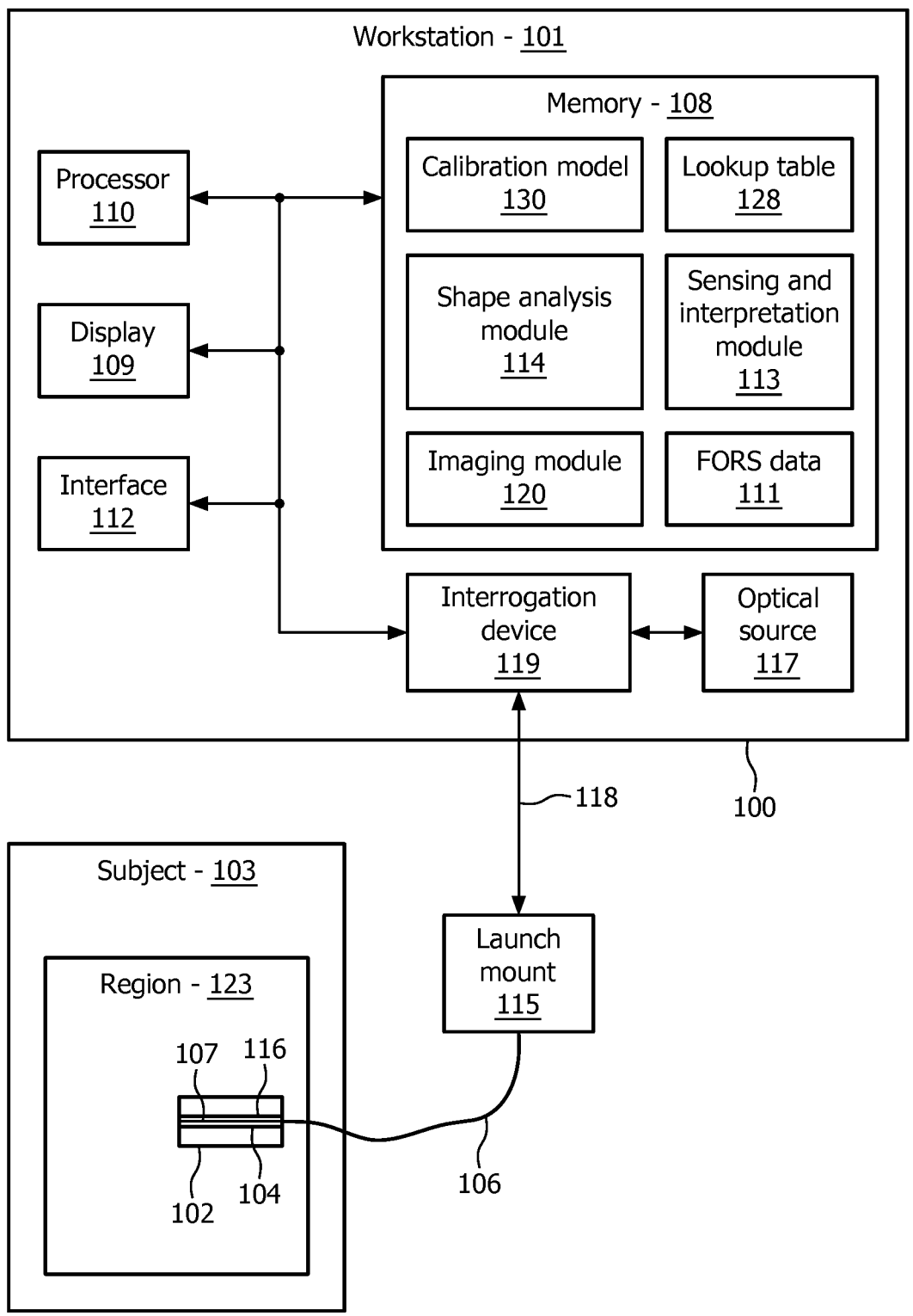
FIG. 1 is a block/flow diagram showing a system for tracking and determining characteristics of inflatable medical instruments using FORS data in accordance with one illustrative embodiment.

In accordance with the present principles, a system for tracking and determining characteristics of inflatable medical instruments using FORS data is provided. The system includes an inflatable medical instrument that is configured for interventional deployment. A guidewire including an optical fiber is positioned within a lumen of the inflatable medical instrument. A FORS system is configured to measure a shape of the guidewire during the interventional deployment of the inflatable medical instrument. A shape analysis module is configured to analyze the FORS data in order to track the inflatable medical instrument and determine characteristics of the inflatable medical instrument.

The tracking and determination of characteristics of the inflatable medical instrument by a FORS system allows the practitioner to monitor the inflatable medical instrument during inflation, pressurization and depressurization of an interventional procedure resulting in a significant reduction in the required radiation dosage on the subject during inflatable medical instrument-based procedures or assisted therapies. Furthermore, the system allows the FORS to be performed on standard inflatable medical instruments without requiring the instrument to be specially manufactured with an imbedded optical fiber. This provides significant benefits concerning the complexity and cost of manufacture for the inflatable medical instruments of the system. It should be understood, however, that the system described herein equally applies to instruments specially manufactured with an imbedded shape sensor.

It should be understood that the present invention will be described in terms of medical systems. However, the teachings of the present invention are much broader and in some embodiments, the present principles are employed in complex biological or mechanical systems. Furthermore, the present principles are applicable to internal procedures of biological systems in all areas of the body such as the lungs, liver, brain, uterus, gastro-intestinal tract, excretory organs, blood vessels, and any other solid organ tissue, tumor tissue and homogenously or heterogeneously enhancing structures of the body. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Similarly, it will be appreciated that various processes may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

In accordance with the present principles, a system for tracking an inflatable medical instrument and identifying characteristics of the instrument using FORS data is provided. Referring now to the drawings in which like numerals represent the same or similar elements and initially to FIG. 1, a system 100 includes an inflatable medical instrument 102. In one exemplary embodiment, the inflatable medical instrument 102 is a balloon catheter. However, the inflatable medical instrument may be other inflatable devices known in the art which are used for interventional procedures or to assist such procedures. The inflatable medical instrument 102 is configured for interventional deployment on a region 123 of a subject 103. The interventional procedure may be a balloon angioplasty, a drug-eluting balloon procedure or any other known procedures.

As shown in FIG. 1, in one embodiment, the system 100 may include a workstation 101 from which the procedure is supervised and/or managed. The workstation 101 preferably includes one or more processors 110, memory 108 for storing programs and applications and a display 109 which permits a user to view images and interact with the workstation 101. The system 100 may further include an interface 112 which may feature a keyboard, mouse, a joystick, a haptic device, or any other peripheral or control to permit user feedback from and interaction with the workstation 101.

In one embodiment, the medical instrument includes at least one lumen 116. A guidewire 104 or like device is positioned within the lumen 116. The guidewire 104 may be positioned within the central lumen of a balloon catheter. In such embodiment, the system may include a standard balloon catheter and an inflatable medical instrument having a specially configured lumen for receiving the guidewire is not required.

A Fiber-Optical RealShape™ sensor is integrated within the guidewire. A Fiber-Optical RealShape system ("FORS") is a commercial name for systems developed by Koninklijke Philips, N.V. As used herein, the terms FORS and FORS systems are not, however, limited to products and systems of Koninklijke Philips, N.V., but refer generally to fiber optic(al) shape sensing and fiber optic(al) shape sensing systems, fiber optic(al) 3D shape sensing, fiber optic(al) 3D shape sensing systems, fiber optic(al) shape sensing and localization or the like. The FORS systems are also commonly known as "optical shape sensing systems" or "optic shape sensing systems". FORS systems include one or more optical fibers 107 that are integrated within the guidewire in a set pattern or patterns. In one embodiment, the optical fiber may connect to a workstation 101 through a launch mount 115 and cabling 118. The cabling 118 may include fiber optics, electrical connections, other instrumentation, etc., as needed. The cabling 118 interfaces with an optical interrogation device 119 that may include or work with an optical source or sources 117. The system may include a sensing and interpretation module 113 that is configured to receive the FORS data 111 and interpret this information. The FORS data 111 may be stored in the memory 108 of the system.

A FORS system uses light from the interrogator device along an optical fiber, such as a multicore optical fiber, for device localization and navigation during surgical intervention. FORS data may be used in combination with real-time or pre-operative images of the medical device to provide improved tracking of the device. The shape along the optical fiber begins at a specific point along the sensor, known as the launch or zero position, and the subsequent shape position and orientation are relative to that point.

The FORS system 106 with fiber optics may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, the measurand (e.g., strain) causes a shift in the Bragg wavelength.

One advantage of this technique is that various sensor elements can be distributed over the length of a fiber. Incorporating three or more cores with various sensors (gauges) along the length of a fiber that is embedded in a structure permits a three-dimensional form of such a structure to be precisely determined, typically with better than 1 mm accuracy. Along the length of the fiber, at various positions, a multitude of FBG sensors can be located (e.g., 3 or more fiber sensing cores). From the strain measurement of each FBG, the curvature of the structure can be inferred at that position. From the multitude of measured positions, the total three-dimensional form is determined.

As an alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length.

Sensors using technology based on Raman scattering, Brillouin scattering, fluorescence scattering or the like may also be used in accordance with the present invention.

By using this effect in three or more cores running within a single length of multi-core fiber, the 3D shape and dynamics of the surface of interest can be followed. While the preferred embodiments describe the optical fiber for the FORS system as a multicore optical fiber, discrete optical fibers may be utilized for the FORS system in other embodiments. Furthermore, while the system 100 is illustratively described as utilizing a FORS system 106, other known shape sensor systems and sensors may be utilized for the system in accordance with the present principles.

Figure 2:
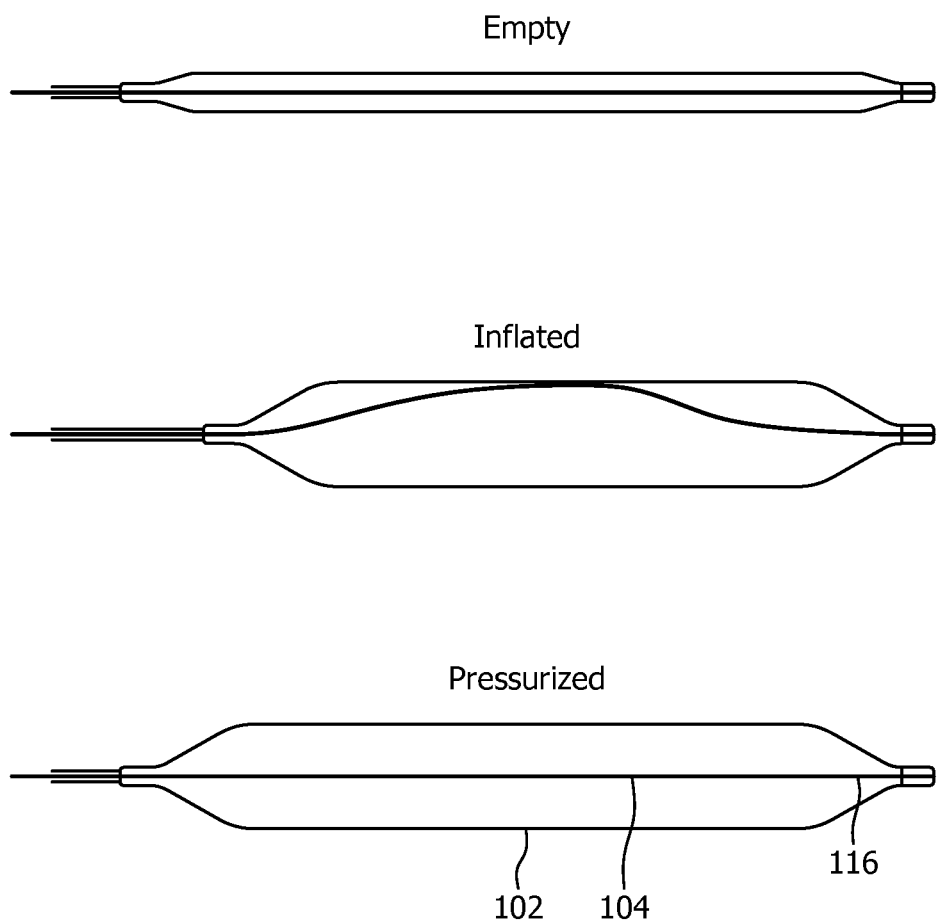
FIG. 2 shows images of a guidewire within an inflatable medical instrument.

The system 100 may be configured to locate the segment of the optical fiber 107 of the FORS system that is contained within the balloon, such as by a longitudinal encoding device or other means known in the art. The FORS system allows for determination of the shape of the guidewire 104 during an interventional procedure. For example, a balloon catheter during balloon angioplasty will display various configurations which will result in characteristic changes in the shape of the lumen 116. As shown in FIG. 2, the lumen 116 of a balloon catheter during balloon angioplasty is relatively linear when the balloon is empty. However, during the inflation and pressurization of the balloon catheter, the shape of the lumen 116 of the balloon exhibits significant deformations. More specifically, when the balloon catheter is being initially filled with fluid, the guidewire lumen buckles and transitions from a straight lumen to a curved lumen. Later in the procedure, when the balloon is filled with fluid and is in an unpressurized state, the central lumen exhibits a maximum curvature. Once the balloon is pressurized, the curvature of the lumen is reduced and the lumen 116 returns to a relatively linear configuration.

Figure 3:
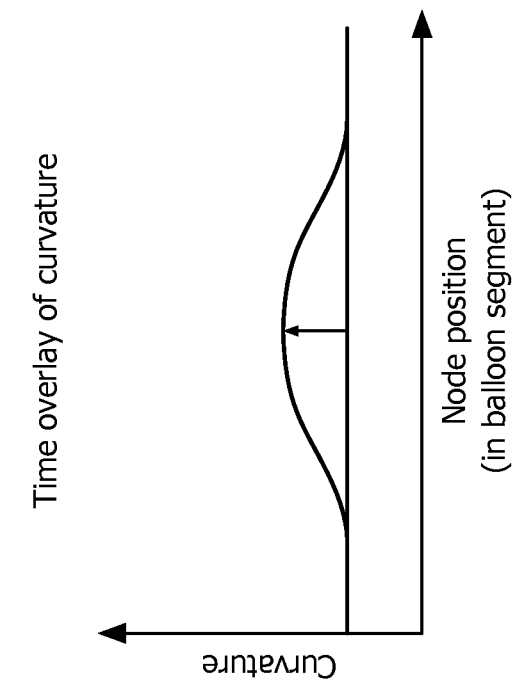
FIG. 3 shows images of a guidewire within an inflatable medical instrument as well as a graph displaying a time overlay of curvature for the inflatable medical instrument.
Figure 3:
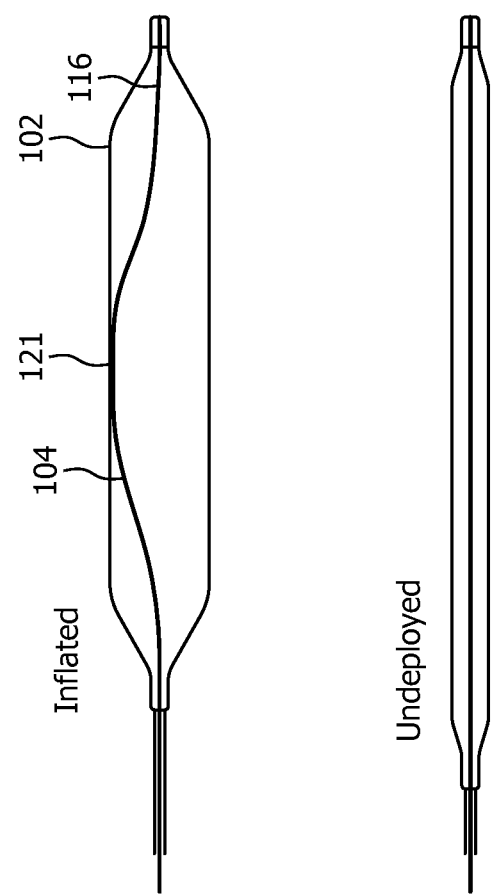

As shown in FIGS. 2 and 3, these changes in the shape of the lumen 116 result in corresponding changes in the shape of the guidewire within the lumen. The FORS system 106 of the present invention detects the shape of the guidewire and tracks these changes during an interventional procedure. The changes in shape of the guidewire can then be used for determining numerous characteristics of the medical instrument including the orientation, position, pressurization and/or the status of the inflatable medical instrument. For example, during a balloon angioplasty, the shape of the guidewire 104 within a lumen 116 of the balloon catheter will be indicative of the diameter of the balloon during inflation and deflation of the device. The shape of the guidewire 104 will also indicate whether the balloon is pressurized or unpressurized. As shown in FIG. 2, if the balloon is not pressurized after inflation, the guidewire 104 will be curved whereas the guidewire will be linear if the balloon is pressurized after inflation. As will be explained herein, the analysis of FORS data concerning the guidewire 104 also allows the determination of the position of the inflatable medical instrument 102 and provides the status of the balloon concerning rupture.

Figure 4:
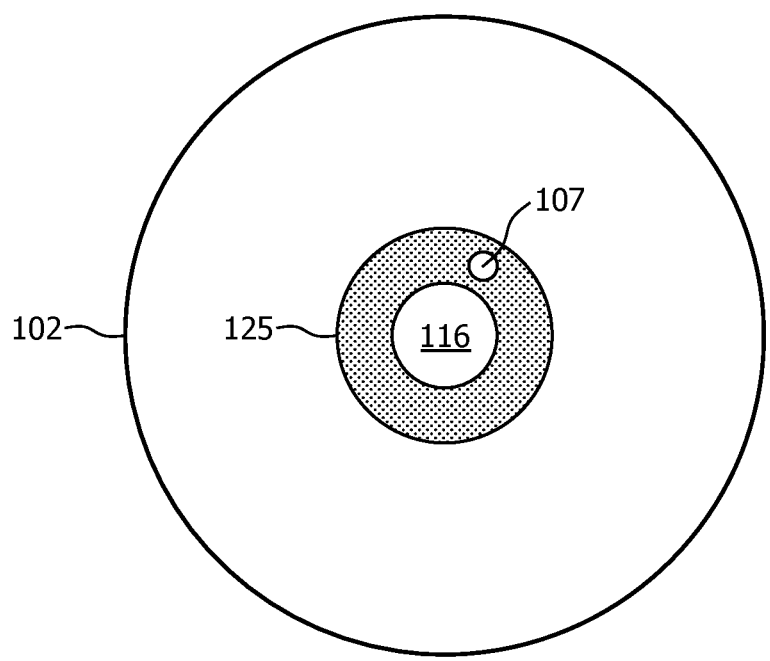
FIG. 4 shows images of an inflatable medical instrument having an imbedded shape sensor.

Furthermore, in an alternative embodiment shown in FIG. 4, the optical fiber 107 of the FORS system may be imbedded directly within the body of the inflatable medical instrument 102, which is shown in an inflated state. For example, the optical fiber 107 may be integrated within the wall 125 of the catheter lumen. In these embodiments, the FORS data provides direct information concerning the changes in the shape of the inflatable medical instrument and the FORS data may be similarly utilized to determine numerous characteristics of the medical instrument as well as provide the state of the medical instrument, the position of the inflatable medical instrument and provide the status of the balloon concerning rupture.

The system further includes a shape analysis module 114 which is configured to receive the FORS data 111 from the FORS system 106, analyze the FORS data and determine one or more characteristics of the inflatable medical instrument. As shown in FIG. 1, in one embodiment, the shape analysis module 114 may be integrated within the workstation 101. However, in other embodiments, the shape analysis module 114 may comprise an external device and may not be integrated within the workstation.

In one embodiment, the shape analysis module 114 is configured to determine the characteristics of the inflatable medical instrument by computing the curvature for the section of the optical fiber in the balloon or other inflatable structure. The shape analysis module is configured to determine characteristics of the inflatable medical instrument for any sequence of pressure changes during an interventional procedure.

In one embodiment, the shape analysis module 114 may be configured to analyze the plot indicative of the curvature response of the balloon by computing the cumulative area under the plot. This area provides information concerning the changes in the shape of the guidewire 104 and allows the shape analysis module 114 to determine characteristics of the inflatable medical instrument.

The shape analysis module 114 is configured to receive the FORS data and determine changes in the shape by measuring parameters of the shape of the guidewire 104 including the three-dimensional shape, two-dimensional projection of the shape, curvature, alpha, axial strain, etc. The shape analysis module 114 is also configured to compute an instantaneous virtual measurement of both balloon diameter and pressure using the computed change in the shape. The shape analysis module 114 is also configured to compute the number of inflation cycles during the interventional procedure based upon the FORS data.

The actual balloon pressure and the shape response may have a complex relationship. Therefore, in one embodiment, a calibration for each model of an inflatable medical instrument is developed using a measured parameter, such as curvature, in response to a pressure change. The shape analysis module 114 is configured to use the model 130 in order to compute a calibrated determination of the characteristics of the instrument. A calibration based on the specific model of the inflatable medical instrument being tracked is likely necessary only once for each model of the inflatable medical instrument because parameters are likely to be consistent across all instances of the same model.

In one embodiment, the system 100 is configured to automatically determine the model of the inflatable medical instrument 102 such as by RFID or other means for automatic detection. The system 100 may include a stored balloon lookup table 128 for determining the model of the inflatable medical instrument 102. Alternatively, a user may input the specific model into the system 100 by the interface 112.

Figure 5:
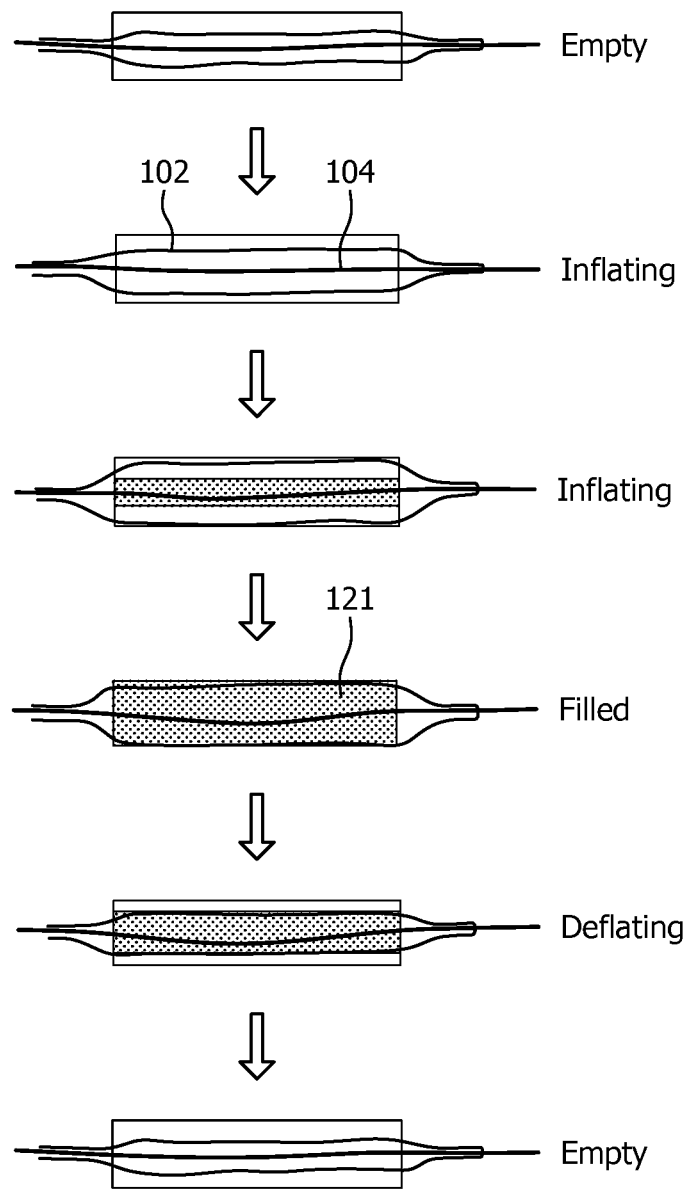
FIG. 5 shows images of a guidewire within an inflatable medical instrument which includes overlays indicating the state of inflation.
Figure 11:
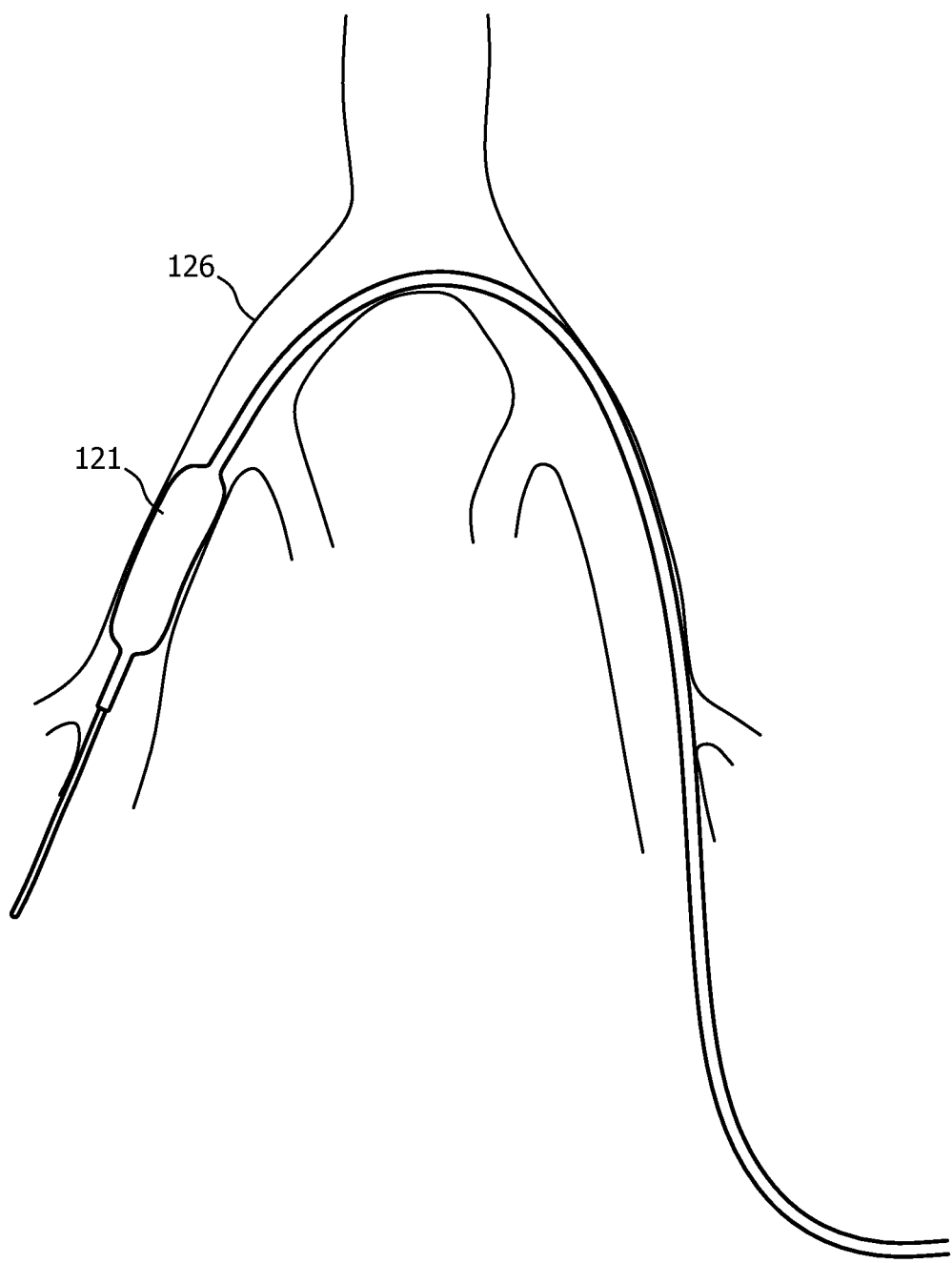
FIG. 11 shows a visual model of an inflatable medical instrument overlaid on an intraoperative image.

The system 100 may further comprise an imaging module 120 which is configured to generate graphical models of the inflatable medical instrument 102 and other images based on the characteristics determined by the shape analysis module 114. In one embodiment, the parameters of the generated image may be further updated based on additional data such as information obtained via fluoroscopy or another imaging modality or due to a user input. The images are preferably overlaid on live or pre-operative images. For example, in FIG. 5, an overlay 121 indicating the balloon diameter as determined by the shape analysis module 114 is generated and displayed over images of the inflatable medical instrument. As shown in FIG. 3, the imaging module 120 may also be configured to generate a graphical representation of the orientation of the guidewire 104 based on the FORS data 111. FIG. 11 shows a visual three-dimensional model of an inflatable medical instrument 102 (FIG. 3) overlaid on an intraoperative image 126.

As shown in FIG. 1, in one embodiment, the imaging module 120 may be integrated in the workstation 101. However, in other embodiments, the imaging module 120 may comprise an external device and may not be integrated within the workstation 101.

The images of the inflatable medical instrument 102 may be acquired by a variety of imaging modalities known in the art that are employed during the interventional procedure to provide real-time or pre-operative images. In such embodiments, the guidewire 104 may be registered to the patient system and the imaging system. The images may be stored in the memory 108 of the system 100 and generated on the display 109 in combination with the overlay 121 generated by the imaging module 120. In the embodiment shown in FIG. 5, the width of the overlay 121 is directly proportional to the balloon diameter measured by the shape analysis module.

Figure 6:
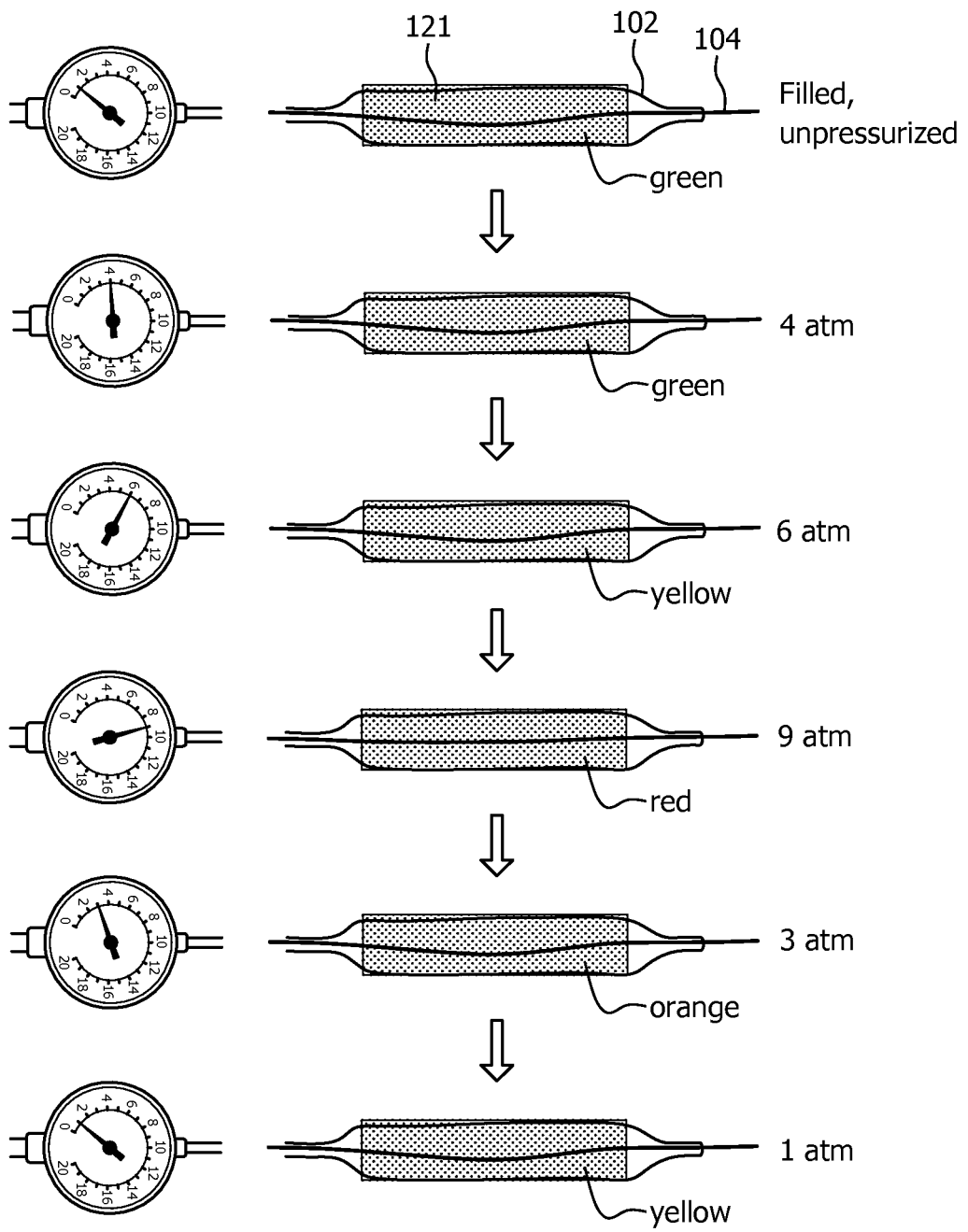
FIG. 6 shows images of a guidewire within an inflatable medical instrument which includes overlays indicating the state of pressurization and images of the actual pressure measurement for the instrument.

As shown in FIGS. 3 and 6, the overlays 121 may be color coded. For example, the overlays in FIGS. 3 and 6 may have a green color to indicate low pressure conditions and a red color to indicate high pressure conditions for the inflatable medical instrument. The overlay 121 in FIG. 6 provides a clear visual guide concerning the real-time state of pressurization of the balloon catheter for the practitioner during an interventional procedure. The color of the overlay 121 also provides a clear warning to the practitioner concerning the existence of a high pressure condition in the medical instrument. The color mapping of the overlay can be specific to each balloon model (nominal pressure, burst pressure).

Figure 7:
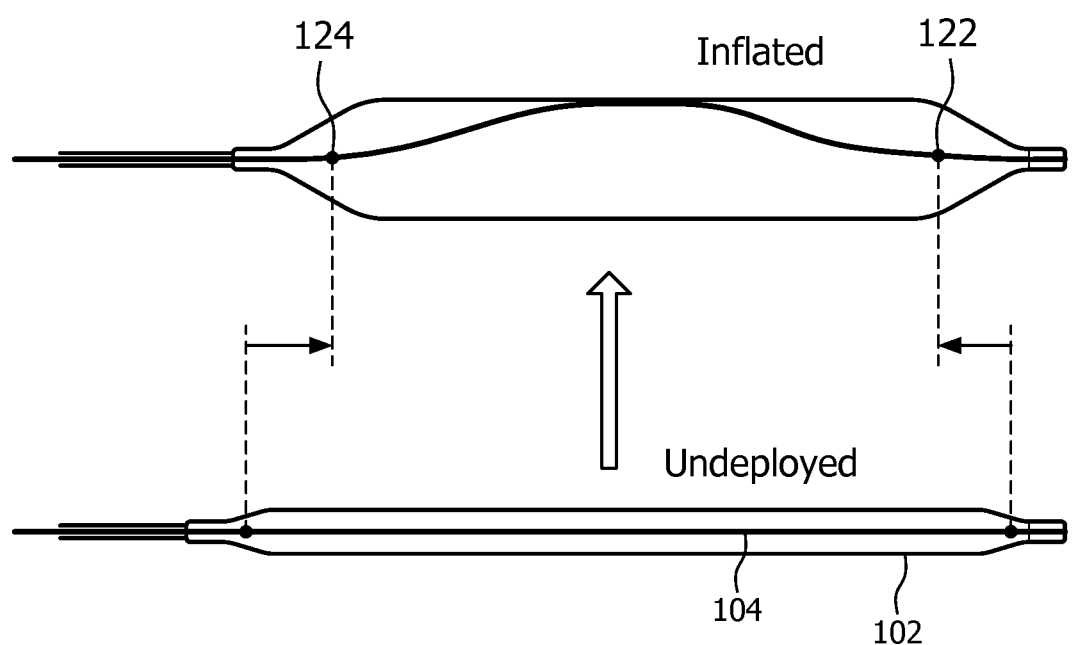
FIG. 7 shows images of a balloon catheter which is analyzed based on three-dimensional point tracking.

In another embodiment, the shape analysis module 114 is configured to analyze the FORS data 111 and determine one or more characteristics of the inflatable medical instrument by three-dimensional point tracking. More specifically, as shown in FIG. 7, the shape analysis module 114 is configured to identify a point 122 at the beginning and at the end 124 of the medical device. These points may be input into a workstation 101 by the user through the interface 112. Alternatively, the points 122, 124 may be automatically identified by the system based on structural and/or positional characteristics of the inflatable medical instrument 102.

The shape analysis module 114 is configured to determine the linear distance between the points 122, 124. During the interventional procedure, the shape analysis module 114 tracks points 122, 124 for changes in the linear distance between them. The changes in the length of the lumen between the two points 122, 124 in response to changes in the inflatable medical instrument 102 are analyzed by the shape analysis module 114 and characteristics concerning the medical instrument are determined based on these changes.

For example, as shown in FIG. 7, the distance between two points 122, 124 at the beginning and end of a balloon catheter decreases as the balloon catheter inflates during a balloon angioplasty. This change in distance is then utilized by the shape analysis module to determine characteristics concerning the inflatable medical instrument. For instance, the diameter of the balloon catheter during a balloon angioplasty procedure may be obtained by analyzing the distance of the two points. A calibration model may be utilized for increased accuracy of the determinations by the shape analysis module 114. Calibrated models 130 may be in the form of a linear, polynomial, exponential, logarithmic, or other relationship, a lookup table 128, or some combined relationship thereof that relates a shape-derived calculation to the actual balloon state. Distance changes may be tracked by the shape analysis module 114 utilizing three-dimensional point tracking.

Figure 8:
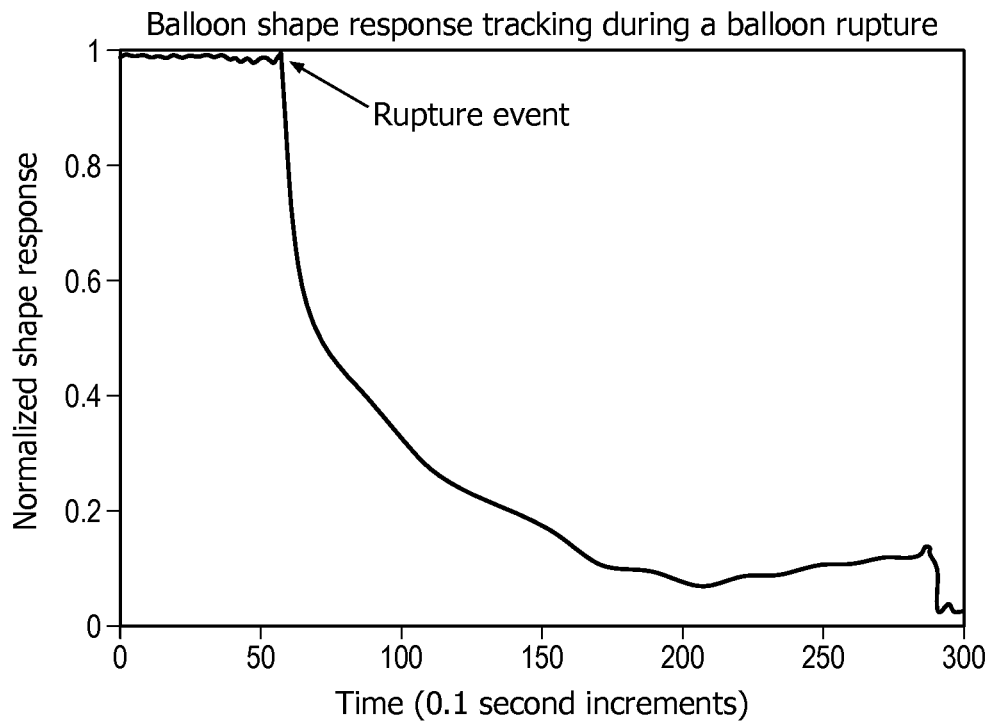
FIG. 8 shows a graph concerning shape response tracking of the inflatable medical instrument during a rupture.

The shape analysis module 114 is also configured to determine the status of the balloon concerning rupture based on the FORS data 111. More specifically, by monitoring the rate of changes of the inflatable medical instrument 102 concerning diameter and pressurization by analysis of the FORS data 111, an adverse event such as rupture may be detected by a high rate of change in these characteristics. For example, FIG. 8 shows a graph of the normalized shape response of a balloon catheter before and after a balloon catheter rupture. After the rupture event, an approximate 50% decrease of the total response is exhibited within the first 30 milliseconds after the rupture. In one embodiment, the system 100 may include a threshold value for the rate of a decrease in the shape response of a particular inflatable medical instrument. If the measured rate of a decrease in the shape response exceeds the threshold value, this indicates that there has been a rupture of the inflatable medical instrument. In some embodiments, the system 100 is configured to produce an optical or auditory signal when a rupture is detected by the shape analysis module 114.

The shape analysis module 114 is also configured to utilize the FORS data 111 to determine the position of the inflatable medical instrument 102. The localized shape change of the guidewire 104 based on the changes in the balloon lumen has a much higher amplitude than shape change in the surrounding areas of the subject during the inflation of device. The shape analysis module 114 is configured to receive an input from the user indicating that the inflation has begun. The shape analysis module then selects a baseline frame for the inflatable medical instrument for comparison. The shape analysis module 114 compares the curvature or other shape parameters during the procedure and computes a position of the inflatable medical instrument.

Figure 9:
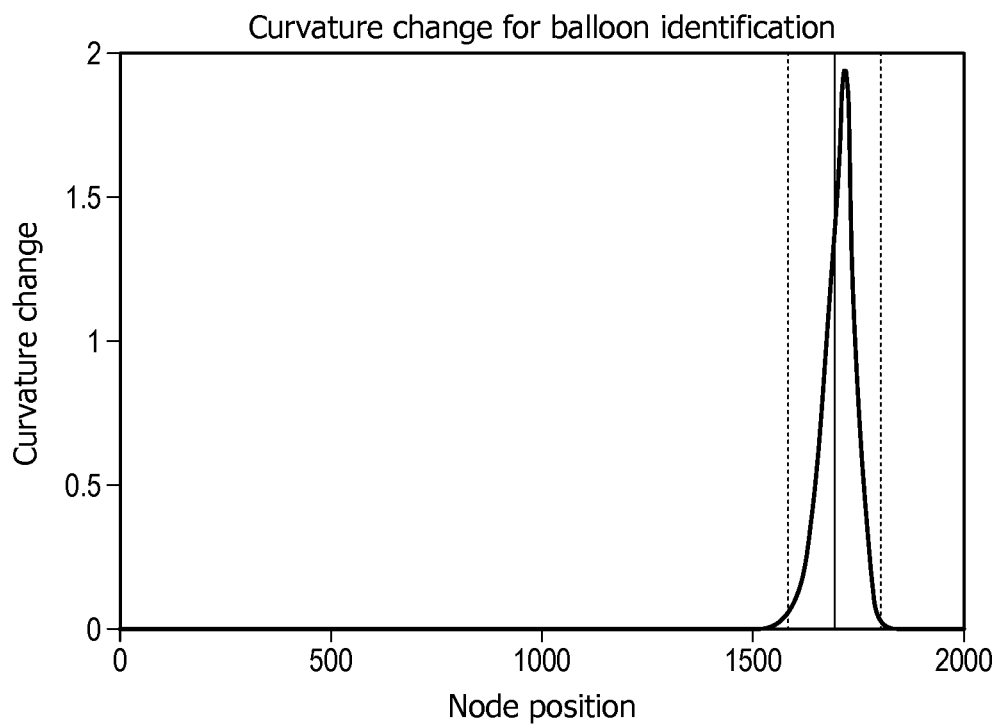
FIG. 9 shows a graph concerning curvature of the inflatable medical instrument and the surrounding area for determining the position of the inflatable medical instrument.

FIG. 9 shows a graph of the curvature change for identification of the balloon position along the guidewire. The balloon position can be estimated by its endpoints, which are found to be the first point before and after the peak that drops below a certain threshold value determined by a balloon calibration. The center position of the balloon along the guidewire is identified as halfway between these points. In one embodiment, using the known length of the balloon, the distance between the beginning and end point is determined by the shape analysis module 114 and a confidence score for the accuracy of the detected balloon position is generated. The position of the inflatable medical instrument may be used by the shape analysis module 114 to visualize the instrument and to register the position of the instrument in a global coordinate system for tracking purposes. The imaging module 120 may generate a graphical representation of the inflatable medical instrument 102 using the determined position of the instrument. In another embodiment, the balloon position is identified using a longitudinal encoding device.

In the alternative embodiment shown in FIG. 4 wherein the optical fiber of the FORS system is imbedded directly within the body of the inflatable medical instrument, the system 100 utilizes the FORS data to determine characteristics of the inflatable medical instrument 102 in a similar manner as described for the embodiments in which the optical fiber is within the guidewire 104.

Figure 10:
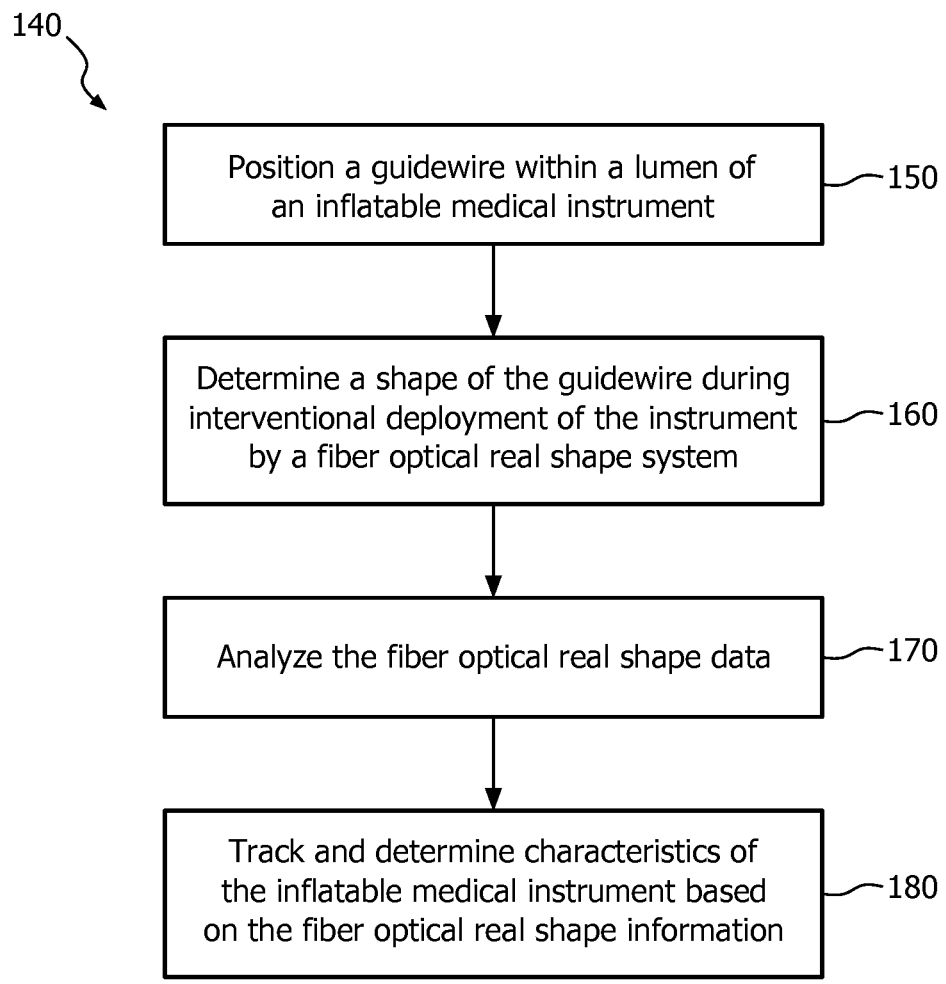
FIG. 10 is a flow diagram showing a method for tracking and determining characteristics of an inflatable medical instrument.

Referring to FIG. 10 methods 140 for tracking an inflatable medical instrument 102 that is configured for an interventional procedure and determining characteristics of the instrument are illustratively shown in accordance with the present principles. In block 150, a guidewire 104 is positioned within a lumen 116 of an inflatable medical instrument. In block 160, a shape of the guidewire during an interventional procedure is determined by a FORS system.

In block 170, the FORS data 111 from the FORS system is analyzed. For example, the FORS data 111 may be analyzed by a computation using curvature data or three-dimensional point tracking data for the inflatable instrument, as previously described with respect to the system 100 of the present invention.

In block 180, the inflatable medical instrument is tracked and characteristics of the inflatable medical instrument are determined based upon the FORS data 111 from the FORS system. For example, characteristics including the diameter of the inflatable instrument, the pressurization of the instrument and whether the instrument has ruptured may be determined in a manner previously described for the system 100 of the present invention. The position of the instrument may also be determined in order to track the instrument and register the instrument in a global coordinate system.

In one embodiment, the method includes the additional step of generating images based on the characteristics of the inflatable medical instrument. The images that are generated may be an overlay, a virtual image of the guidewire, a virtual image of the inflatable medical instrument, etc.

Figure 12:
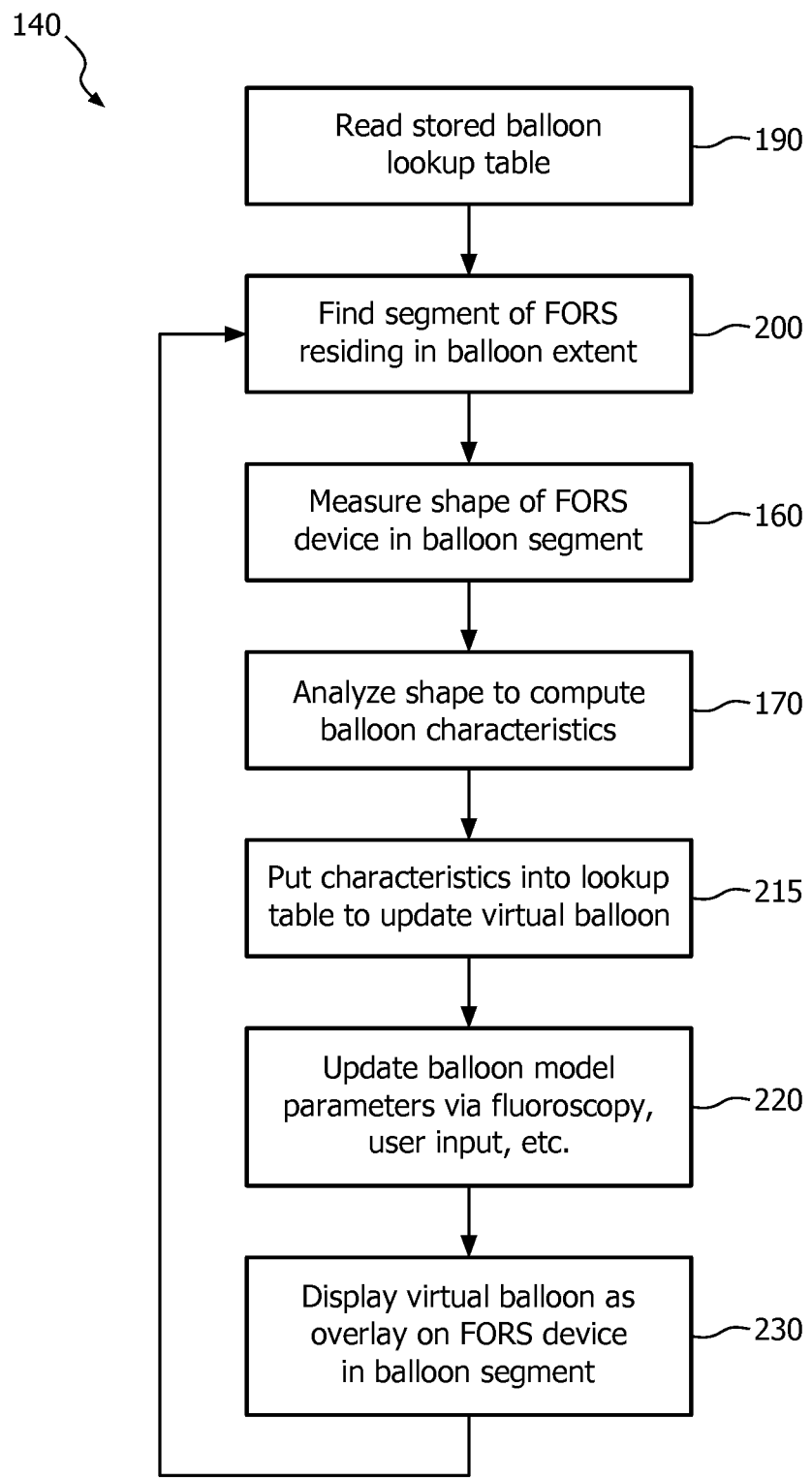
FIG. 12 is a flow diagram showing another embodiment of the method for tracking and determining characteristics of an inflatable medical instrument.

FIG. 12 shows another embodiment of the method 140 for tracking an inflatable medical instrument 102 that is configured for an interventional procedure and determining characteristics of the instrument in accordance with the present principles. In block 190, a stored lookup table is read in order to determine the model of the inflatable medical instrument. The lookup table is preferably stored in the memory 108 of the workstation 101.

In block 200, a segment of the optical fiber 107 of the FORS system 106 is located in the inflatable medical instrument during an interventional procedure. The optical fiber may be integrated in a guidewire that is positioned in the lumen of the inflatable medical instrument or the optical fiber may be imbedded directly in the inflatable medical instrument. In one embodiment, a longitudinal encoding device and method is used to locate the optical fiber within the guidewire positioned in the lumen 116 of the inflatable medical instrument. In block 160, a shape of the FORS device in the inflatable medical instrument during an interventional procedure is determined by a FORS system.

In block 170, the FORS data 111 from the FORS system is analyzed and characteristics of the inflatable medical instrument are determined based upon the FORS data 111 from the FORS system. In block 215, the characteristics determined from the FORS data are input into the lookup table and the display of a virtual balloon is updated. In block 220, the balloon model parameters may be further updated such as via fluoroscopy or user input. In block 230, the virtual balloon is displayed as an overlay on the FORS device in the balloon segment. The overlay may be displayed on live or pre-operative images.

Figure 13:
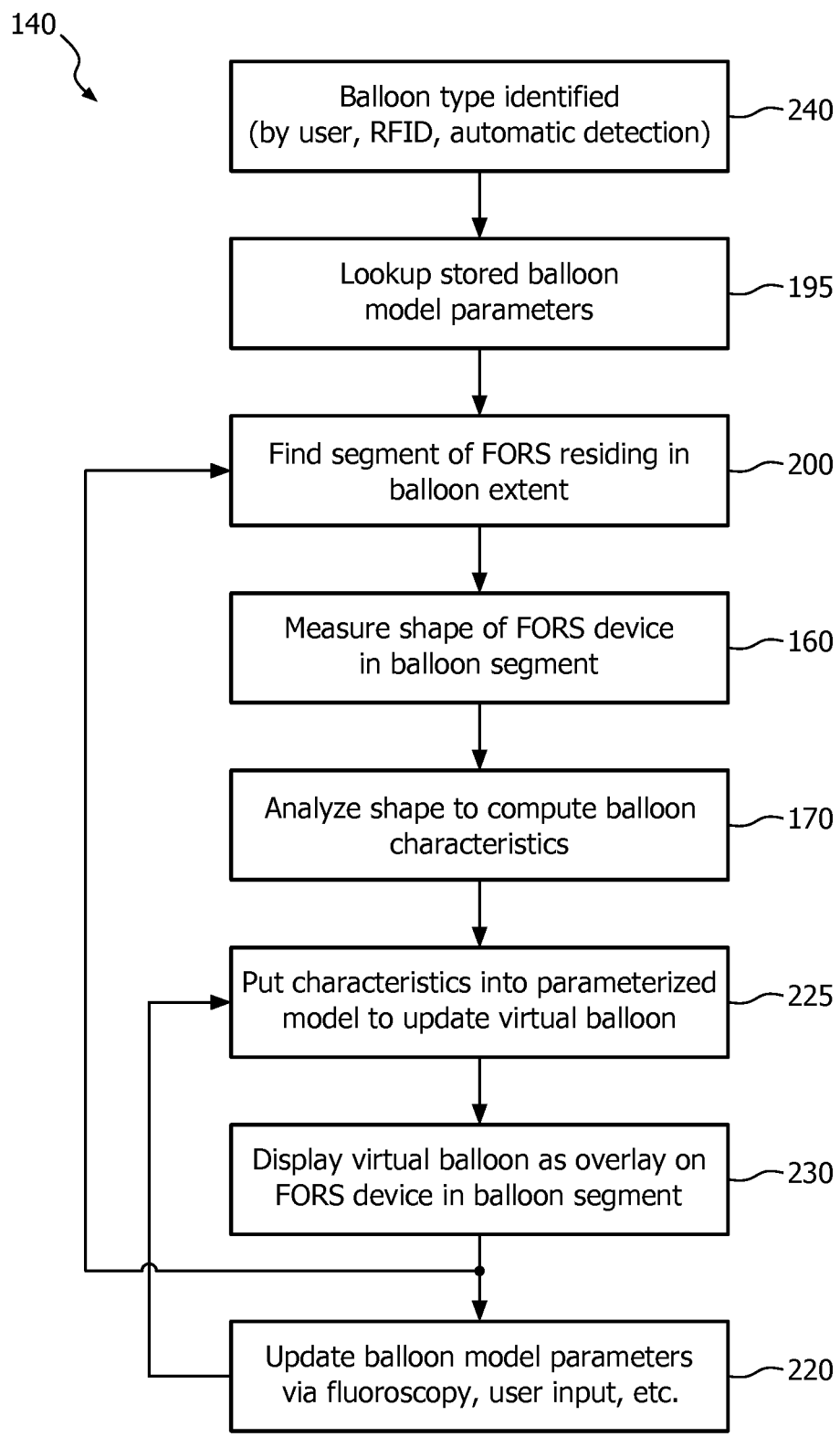
FIG. 13 is a flow diagram showing another embodiment of the method for tracking and determining characteristics of an inflatable medical instrument.

FIG. 13 shows another embodiment of the method 140 for tracking an inflatable medical instrument 102 that is configured for an interventional procedure and determining characteristics of the instrument in accordance with the present principles. In block 240, the model type of the inflatable instrument is identified either by the user, RFID technology or automatic detection. In block 195, stored model parameters are read in order to determine the parameters for the model of the inflatable medical instrument. In block 200, a segment of the optical fiber 107 of the FORS system 106 is located in the inflatable medical instrument during an interventional procedure by a longitudinal encoding device and method or by other means known in the art. In block 160, a shape of the FORS device within the inflatable medical instrument during an interventional procedure is determined by a FORS system.

In block 170, the FORS data 111 from the FORS system is analyzed and characteristics of the inflatable medical instrument are determined based upon the FORS data 111 from the FORS system. In block 225, the characteristics determined from the FORS data are placed into a parameterized model to update a display of a virtual balloon. In block 230, the virtual balloon is displayed as an overlay on the FORS device in the balloon segment. The overlay may be displayed on live or pre-operative images. In block 220, the balloon model parameters may be further updated such as via fluoroscopy or user input.

These methods for tracking and determining characteristics of the inflatable medical instrument by a FORS system may result in a reduction in the required radiation dosage for the subject during inflatable medical instrument-based procedures or assisted therapies. Furthermore, the methods which integrate the FORS device in the guidewire allow FORS to be used on standard inflatable medical instruments without requiring the instrument to be specially manufactured with an imbedded optical fiber. This provides a significant savings in the complexity and cost for manufacturing the inflatable medical instruments associated with the method.

It is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for the system and method for tracking and determining characteristics of inflatable medical instruments using FORS data (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A medical system, comprising:
an inflatable medical instrument configured for interventional deployment, the inflatable medical instrument including a lumen running longitudinally through a central portion of an inflatable structure of the inflatable medical instrument;
a guidewire positioned within the lumen and configured to guide the inflatable medical instrument during the interventional deployment;
an optical shape sensing system comprising an optical fiber integrated in the guidewire, the optical fiber being configured to provide shape sensing data indicating a curvature of the guidewire during the interventional deployment; and
at least one processor and a non-transitory memory for storing instructions that, when executed by the at least one processor, cause the at least one processor to determine inflation and pressurization characteristics of the inflatable structure based on the shape sensing data indicating the curvature of the guidewire within the inflatable structure.

2. The system as recited in claim 1, wherein the instructions cause the at least one processor to further determine at least one of a node distance, axial strain, or three-dimensional shape of the inflatable medical instrument.

3. The system as recited in claim 1, wherein the memory further includes a lookup table or model, wherein the instructions further cause the at least one processor to perform calibration of the inflatable medical instrument using the lookup table or model.

4. The system as recited in claim 1, wherein the instructions further cause the at least one processor to detect when the inflatable medical instrument has ruptured, and to produce a signal when a rupture is detected.

5. The system as recited in claim 1, wherein the instructions further cause the at least one processor to generate a graphical model of the inflatable medical instrument based on the determined characteristics, and to update the graphical model based on data from an imaging modality or due to a user input.

6. The medical system as recited in claim 1, wherein the optical fiber is integrated within a wall of the lumen.

7. The medical system as recited in claim 1, wherein determining the characteristics of the inflatable medical instrument comprises determining whether the inflatable medical instrument is pressurized or unpressurized when inflated.

8. The medical system as recited in claim 7, wherein determining the characteristics of the inflatable medical instrument comprises determining a diameter of the inflatable medical instrument during inflation and deflation.

9. The medical system as recited in claim 1, wherein the instructions further cause the at least one processor to determine changes in a linear distance between points at opposite sides of the inflatable medical instrument based on the shape sensing data, and to determine the characteristics of the inflatable structure using the determined changes.

10. The system as recited in claim 1, wherein the curvature of the guidewire is substantially linear when the inflatable structure of the medical instrument is uninflated and unpressurized, wherein the curvature of the guidewire is deformed when the inflatable structure of the medical instrument is inflated and unpressurized, and wherein the curvature of the guidewire is substantially linear when the inflatable structure of the medical instrument is inflated and pressurized.

11. A medical system for tracking and determining characteristics of an inflatable medical instrument configured for interventional deployment, the system comprising:

an inflatable medical instrument configured for interventional deployment, and comprising an inflatable structure;

a guidewire positioned within a lumen running longitudinally through a central portion of the inflatable structure of the inflatable medical instrument for guiding the inflatable medical instrument during the interventional deployment, wherein the guidewire exhibits deformations responsive to inflation and pressurization of the inflatable structure of the inflatable medical instrument;

an optical shape sensing system comprising an optical fiber integrated in the guidewire for measuring a shape of the guidewire during the interventional deployment of the inflatable medical instrument; and a workstation including:
one or more processors, and
a non-transitory memory for storing instructions that, when executed by the one or more processors, cause the one or more processors to determine characteristics of the inflatable medical instrument based on a curvature of the guidewire within the inflatable structure indicated by sensing data from the optical shape sensing system.

12. The system as recited in claim 11, wherein the instructions cause the one or more processors to determine the characteristics of the inflatable medical instrument by computing shape parameters for the inflatable medical instrument.

13. The system as recited in claim 11, wherein the memory includes a lookup table or model for calibration of the inflatable medical instrument.

14. The system as recited in claim 11, wherein the instructions further cause the one or more processors to generate a graphical model based on the determined characteristics, and to update the graphical model based on data from an imaging modality or due to a user input.

15. The system as recited in claim 11, wherein the determined characteristics of the inflatable medical instrument comprise a diameter of the inflatable medical instrument, a pressure of the inflatable medical instrument and/or a total number of inflation cycles for the inflatable medical instrument.

16. A method for tracking and determining characteristics of an inflatable medical instrument configured for interventional deployment, the method comprising:

positioning a guidewire within a lumen running longitudinally through a central portion of an inflatable structure of the inflatable medical instrument, the guidewire including an optical fiber for performing optical shape sensing of the guidewire;

guiding the inflatable medical instrument during the interventional deployment using the guidewire;

determining a curvature of the guidewire during the interventional deployment of the inflatable medical instrument using the optical fiber; and determining inflation and pressurization characteristics of the inflatable structure based on the determined curvature of the guidewire within the inflatable structure.

17. The method as recited in claim 16, wherein the characteristics of the inflatable medical instrument comprise diameter of the inflatable medical instrument.

18. A device comprising:

an inflatable medical instrument including an inflatable structure and a lumen running longitudinally through a central portion of the inflatable structure;

a guidewire positioned in the lumen for guiding the inflatable medical instrument during interventional deployment, the guidewire including an optical fiber; and at least one processor and a non-transitory memory for storing instructions that, when executed by the at least one processor, cause the at least one processor to detect from shape sensing data from the optical fiber a shape of the optical fiber, the shape of the optical fiber indicating a curvature of the guidewire within the inflatable structure, and to determine whether the inflatable medical instrument is pressurized after inflation based on the curvature of the guidewire.

19. The device of claim 18, wherein the instructions further cause the at least one processor to determine a diameter of the inflatable medical instrument during the inflation and deflation of the inflatable medical instrument.

* * * * *